United States Patent [19]
de Nanteuil et al.

[11] Patent Number: 5,866,587
[45] Date of Patent: Feb. 2, 1999

[54] METALLOPROTEASE INHIBITORS

[75] Inventors: Guillaume de Nanteuil, Suresnes; Joseph Paladino, Conflans Sainte Honorine; Georges Remond, Versailles; Ghanem Atassi, Saint Cloud; Alain Pierre, Marly le Roi; Gordon Tucker; Jacqueline Bonnet, both of Paris; Massimo Sabatini, Garges, all of France

[73] Assignee: Adir Et Compagnie, Courbevoie, France

[21] Appl. No.: 842,982

[22] Filed: Apr. 25, 1997

[30] Foreign Application Priority Data

Apr. 26, 1996 [FR] France .................. 96 05321

[51] Int. Cl.$^6$ .............. A61K 31/435; C07D 495/04; C07D 491/04
[52] U.S. Cl. .............. 514/302; 546/115; 546/116; 546/114; 546/118; 546/84; 546/86; 546/87; 546/80; 546/89; 546/92; 546/122; 546/123; 546/113; 546/88; 514/301; 514/303; 514/300; 514/292; 514/291
[58] Field of Search .............. 546/114, 115, 546/116; 514/301, 302

[56] References Cited

U.S. PATENT DOCUMENTS

| | | | |
|---|---|---|---|
| 4,193,997 | 3/1980 | Boigegrain et al. | 424/256 |
| 5,672,615 | 9/1997 | MacPherson et al. | 514/357 |

FOREIGN PATENT DOCUMENTS

| | | | |
|---|---|---|---|
| 97/18194 | 5/1997 | WIPO | 217/26 |

OTHER PUBLICATIONS

A.L. Harris, The Lancet, vol. 349, SH 13–15, May, 1997.
M. Skobe, Nature Medicine, vol. 3, No. 11, 1222–1227, Nov. 1997.
J. Nemunaitis, Clinical Cancer Research, vol. 4, 1101–1109, May 1998.
Nagase, H., "Matrix metalloproteinases," in Zinc Metalloproteases in Health and Disease, pp. 177–181, 1996.

*Primary Examiner*—Mukund J. Shah
*Assistant Examiner*—Ann M. Kessinger
*Attorney, Agent, or Firm*—The Firm of Gordon W. Hueschen

[57] ABSTRACT

Compound of formula (I):

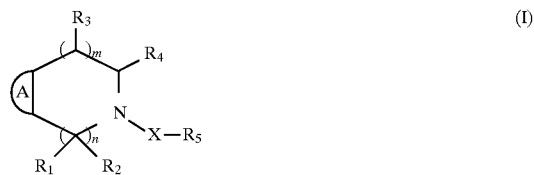

in which:

m, n, which are identical or different, represent 0, 1 or 2, $R_1$, $R_2$, which are identical or different, represent hydrogen, optionally substituted alkyl, aryl, or form with the carbon atom carrying them carbonyl or ($C_3$–$C_7$)cycloalkyl, $R_3$ represents hydrogen, alkyl, hydroxyl or aryl, $R_4$ represents any of the groups as defined in the description, X represents —$SO_2$—, —CO— or —$SO_2NH$—, $R_5$ represents optionally substituted alkyl, ($C_3$–$C_7$) cycloalkyl, aryl or heterocyclic, A represents an aryl ring or a heterocycle, its isomers as well as its addition salts with a pharmaceutically acceptable acid or base and medicinal products containing the same are useful as metalloprotease inhibitors.

8 Claims, No Drawings

METALLOPROTEASE INHIBITORS

BACKGROUND OF THE INVENTION

The present invention relates to new metalloprotease inhibitors.

FIELD OF THE INVENTION

In the physiological state, the synthesis of the connective tissues is in dynamic equilibrium with the degradation of the extracellular matrix. This degradation is due to zinc proteases (metalloproteases) secreted by the cells of the existing matrix: they are, with no limitation being implied, the collagenases (MMP-1), the gelatinases or collagenases of type IV (MMP-2, MMP-9) and the stromelysines (MMP-3).

In the normal state, these catabolic enzymes are regulated at the level of their synthesis and of their secretion, as well as at the level of their extracellular enzymatic activity by naturally-occurring inhibitors such as $\alpha_2$-macroglobulin or TIMP (Tissue Inhibitor of MetalloProteinase) which form inactive complexes with the metalloproteases.

The common point between the pathologies involving these enzymes is a disequilibrium between the activity of the activated enzymes and that of their naturally-occurring inhibitors with, as a consequence, an excessive degradation of the tissues.

The uncontrolled and accelerated degradation of the membranes by the resorption of the extracellular matrix catalyzed by the metalloproteases is a parameter common to several pathological conditions such as rheumatoid arthritis, arthrosis, tumor invasion and growth, including malignant dissemination and the formation of metastases, ulcerations, atherosclerosis and the like.

PRIOR ART DESCRIPTION

Recently, BB94, a metalloprotease inhibitor, has shown an antitumor activity in clinical trials where it proved active on ovarian cancers (Becket et al., DDT 1996, 1 (1), 16).

A metalloprotease inhibitor can therefore be expected to restore the balance between protease and inhibitor and thereby to favorably alter the progression of these pathologies.

A number of metalloprotease inhibitors have been described in the literature. This is the case more particularly for the compounds described in patents WO 95/35275, WO 95/35276, EP 606046 or WO 96/00214.

DETAILED DESCRIPTION OF THE INVENTION

The compounds of the present invention, in addition to the fact that they are new, have proved to be more potent metalloprotease inhibitors than those described in the literature, which therefore makes them potentially useful for the treatment of cancers, rheumatic diseases such as arthrosis and rheumatoid arthritis, atherosclerosis and the like.

More specifically, the present invention relates to the compounds of the formula (I):

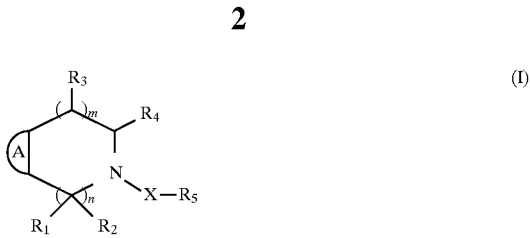

in which:

m, n, which are identical or different, represent 0, 1 or 2, $R_1$, $R_2$, which are identical or different, represent a hydrogen atom, a linear or branched ($C_1$–$C_6$)alkyl group (optionally substituted with an aryl group), an aryl group, or form with the carbon atom carrying them a carbonyl group or a ($C_3$–$C_7$)cycloalkyl group, $R_3$ represents a hydrogen atom, a linear or branched ($C_1$–$C_6$)alkyl group, a hydroxyl group, a linear or branched ($C_1$–$C_6$)alkoxy group or an aryl group, $R_4$ represents any one of the following groups:

- —CO—$NR_6$—$OR'_6$
- —CS—$NR_6$—$OR'_6$
- 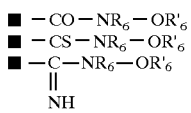

in which:

$R_6$ and $R'_6$, which are identical or different, represent a hydrogen atom or a linear or branched ($C_1$–$C_6$)alkyl group,

- —$CO_2R_7$
- —NH—CO—NH—OH
- —NH—$CH_2$—$CO_2R_7$
- 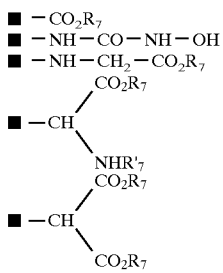

in which:

$R_7$, $R'_7$, which are identical or different, represent a hydrogen atom or a linear or branched ($C_1$–$C_6$)alkyl group (optionally substituted with an aryl group), X represents —$SO_2$—, —CO— or —$SO_2$NH—, $R_5$ represents:
a linear or branched ($C_1$–$C_6$)alkyl group, optionally substituted with one or more halogen atoms or hydroxyl groups, linear or branched ($C_1$–$C_6$)alkoxy groups, aryl groups or —$CO_2R_7$ groups (in which $R_7$ has the same meaning as above),
a ($C_3$–$C_7$)cycloalkyl group,
an aryl group,
or a heterocyclic group, A represents an aryl ring (provided that this aryl ring is different from a phenyl ring when X represents $SO_2$, m and n represent simultaneously the number 1, $R_4$ represents —CO—NHOH, and $R_5$ represents an aryl group or a heterocyclic group), or a heterocycle, their isomers as well as their addition salts with a pharmaceutically acceptable acid or base.

Among the pharmaceutically acceptable acids, there may be mentioned, with no limitation being implied, hydrochloric, hydrobromic, sulfuric, phosphonic, acetic, trifluoroacetic, lactic, pyruvic, malonic, succinic, glutaric, fumaric, tartaric, maleic, citric, ascorbic, oxalic, methanesulfonic and camphoric acids and the like. Among the pharmaceutically acceptable bases, there may be mentioned, with no limitation being implied, sodium hydroxide, potassium hydroxide, triethylamine, tert-butylamine and the like.

Aryl group is understood to mean phenyl, naphthyl, tetrahydronaphthyl, each of these groups being optionally substituted with one or more halogen atoms or a linear or branched ($C_1$–$C_6$)alkyl group, a linear or branched ($C_1$–$C_6$) trihaloalkyl group, a ($C_3$–$C_7$)cycloalkyl group, a ($C_5$–$C_{10}$) bicycloalkyl group, an optionally substituted phenyl group, an optionally substituted pyridyl group, an optionally substituted pyrimidyl group, a linear or branched ($C_1$–$C_6$) alkoxy group (optionally substituted with an amino group itself optionally substituted with one or two alkyl group), a linear or branched ($C_1$–$C_6$)trihaloalkoxy group, a hydroxyl group, a cyano group or an amino group (optionally substituted with one or more linear or branched ($C_1$–$C_6$)alkyl groups).

Heterocycle is understood to mean a saturated or unsaturated 5- to 16-membered mono- or bicyclic group containing one, two or three heteroatoms chosen from oxygen, nitrogen or sulfur, it being understood that the heterocycle may be optionally substituted with one or more halogen atoms or linear or branched ($C_1$–$C_6$)alkyl groups (optionally substituted with an aryl group), linear or branched ($C_1$–$C_6$) alkoxy groups, hydroxyl groups, trihalomethyl groups or amino groups (optionally substituted with one or more linear or branched ($C_1$–$C_6$)alkyl groups).

The preferred compounds according to the invention are those for which:

A represents an aryl ring chosen from phenyl or naphthyl, substituted or unsubstituted, or a heterocycle chosen from thiophene, indole, furan, benzo[b]thiophene, imidazole, pyridine, benzofuran, pyrrole and quinoline rings, substituted or unsubstituted.

The preferred compounds according to the invention are those for which X represents $SO_2$, m is equal to 1, n is equal to 1, $R_1$, $R_2$ and $R_3$ represent simultaneously a hydrogen atom.

The preferred $R_4$ substituents according to the invention are the groups —CO—$NR_6$—$OR'_6$.

The preferred $R_5$ substituents according to the invention are aryl groups or heterocyclic groups and most preferentially phenyl optionally substituted, naphthyl optionally substituted or pyridyl optionally substituted.

The invention also extends to the process for the preparation of the compounds of formula (I), wherein there is used as starting material an acid of formula (II), in racemic form or in the form of a defined isomer:

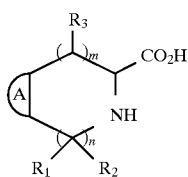
(II)

in which $R_1$, $R_2$, $R_3$, m, n and A have the same meaning as in the formula (I), whose amine functional group is substituted with a halogenated derivative of formula (III):

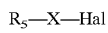
$R_5$—X—Hal (III)

in which X and $R_5$ have the same meaning as in the formula (I) and Hal represents a halogen atom, to give the compound of formula (I/a), which is a specific case of the compounds of formula (I):

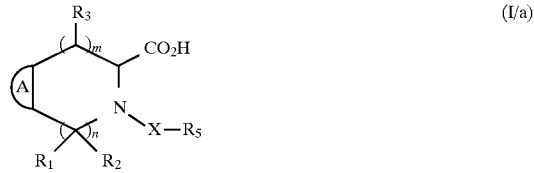
(I/a)

in which A, $R_1$, $R_2$, $R_3$, $R_5$, X, m and n have the same meaning as in the formula (I), a compound of formula (IIa):
(a) whose acid functional group is converted, if desired, to the corresponding ester functional group,
(b) or which is reacted with an O-substituted hydroxylamine to give, after deprotection of the hydroxylamine functional group and possible substitution of the hydroxylamine functional group, the compound of formula (I/b), which is a specific case of the compounds of formula (I):

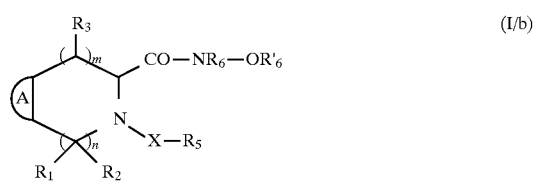
(I/b)

in which A, $R_1$, $R_2$, $R_3$, $R_5$, $R'_6$, $R'_6$, X, m and n have the same meaning as in the formula (I),
a compound of formula (I/b) which is subjected, if desired, to the action of Lawesson's reagent in orthoxylene, to give the compound of formula (I/c), which is a specific case of the compounds of formula (I):

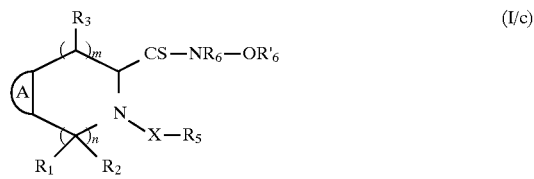
(I/c)

in which A, $R_1$, $R_2$, $R_3$, $R_5$, $R_6$, $R'_6$, X, m and n have the same meaning as in the formula (I),
a compound of formula (I/c) which is subjected, if desired, to the action of ammonium hydroxide, to give the compound of formula (I/d), which is a specific case of the compounds of formula (I):

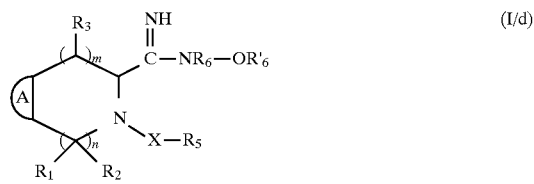
(I/d)

in which A, $R_1$, $R_2$, $R_3$, $R_5$, $R_6$, $R'_6$, X, m and n have the same meaning as in the formula
(c) which is converted to a primary amine of formula (IV):

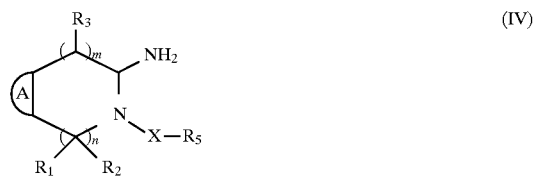
(IV)

in which A, $R_1$, $R_2$, $R_3$, $R_5$, X, m and n have the same meaning as in the formula (I), which is reacted:

either with carbonyldiimidazole and a protected hydroxylamine, to give the compound of formula (I/e), which is a specific case of the compounds of formula (I):

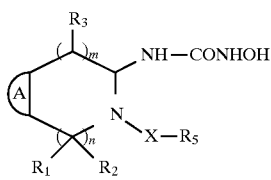

(I/e)

in which A, $R_1$, $R_2$, $R_3$, $R_5$, X, m and n have the same meaning as in the formula (I), or with a bromoacetate, to give the compound of formula (I/f), which is a specific case of the compounds of formula (I):

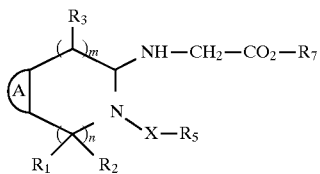

(I/f)

in which A, $R_1$, $R_2$, $R_3$, $R_5$, $R_7$, X, m and n have the same meaning as in the formula (I),
(d) whose acid is reduced to the corresponding alcohol form, and then it is converted to a brominated derivative by the action of $PBr_3$ in ether, to give the compound of formula (V):

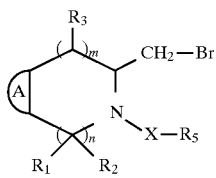

(V)

in which A, $R_1$, $R_2$, $R_3$, $R_5$, X, m and n have the same meaning as in the formula (I), which is reacted:
either with an alkyl malonate, to give, after optional saponification, the compound of formula (I/g):

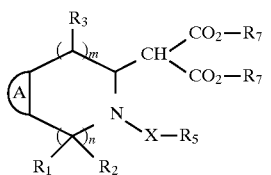

(I/g)

in which A, $R_1$, $R_2$, $R_3$, $R_5$, $R_7$, X, m and n have the same meaning as in the formula (I),
or with a protected glycine, to give, after optional deprotection, the compound of formula (I/h):

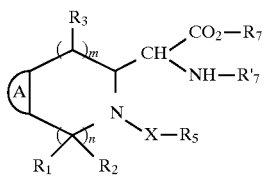

(I/h)

in which A, $R_1$, $R_2$, $R_3$, $R_5$, $R_7$, $R'_7$, X, m and n have the same meaning as in the formula (I),
a compound of formula (I/a) to (I/b), which is purified, where appropriate, according to a conventional purification technique, whose isomers are possibly separated according to a conventional separation technique and which is converted, if desired, to its addition salts with a pharmaceutically acceptable acid or base.

The compounds of formula (II) are either commercially available compounds, or compounds obtained, when n=1, by cyclization of a free amino acid of formula (VI):

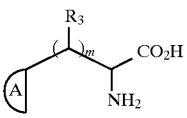

(VI)

in which A, $R_3$ and n have the same meaning as in the formula (I), with a ketone of formula $R_1R_2CO$ in which $R_1$ and $R_2$ have the same meaning as in the formula (I).

The invention also extends to the pharmaceutical compositions comprising, as active ingredient, at least one compound of formula (I) with one or more inert, nontoxic and appropriate excipients. Among the pharmaceutical compositions according to the invention, there may be mentioned more particularly those which are suitable for oral, parenteral (intravenous or subcutaneous) or nasal administration, plain or sugar-coated tablets, sublingual tablets, gelatin capsules, lozenges, suppositories, creams, ointments, skin gels, injectable preparations, oral suspensions and the like.

The useful dosage can be adjusted according to the nature and the seriousness of the condition, the route of administration as well as the age and weight of the patient. This dosage ranges from 0.01 to 2 g per day in one or more doses.

The following examples illustrate the invention but do not limit it in any manner.

The starting materials used are products known or prepared according to known procedures.

The preparations lead to synthesis intermediates which are useful for the preparation of the compounds of the invention.

The structures of the compounds described in the examples and their preparations were determined according to the usual spectrophotometric techniques (infrared, NMR, mass spectrometry and the like).

Preparation A: (6R)-4,5,6,7-Tetrahydrothieno[3,2-c] pyridine-6-carboxylic Acid Hydrochloride

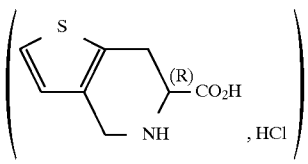

A mixture containing 87 mmol of β-2-thienyl-D-alanine, 11 ml of formaldehyde at 40% in aqueous medium, and 88 ml of 1N hydrochloric acid is heated for 2 h 30 min at 110° C., with stirring, and then at 60° C. overnight. After evaporation, the residue is taken up in ethanol and then evaporated and the expected product is recovered in the form of a solid in diethyl ether.

Melting point: 260° C.

| Elemental microanalysis: | | | | | |
|---|---|---|---|---|---|
| | C % | H % | N % | S % | Cl % |
| Calculated | 43.74 | 4.59 | 6.38 | 14.60 | 16.14 |
| Found | 43.68 | 4.72 | 6.45 | 14.54 | 15.68 |

Preparation B: (3R)-1,2,3,4-Tetrahydro-β-carboline-3-carboxylic Acid

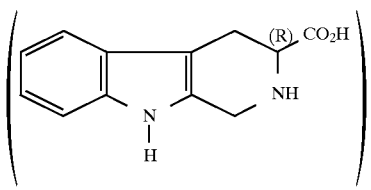

The expected product is synthesized according to the process described by L. Tilstra et al., (J. Am. Chem. Soc., 112, 9176–9182, 1990) from (D)-tryptophan.

Preparation C: (3R)-1,2,3,4-Tetrahydrobenzo[b]thieno[2,3-c]pyridine-3-carboxylic Acid Hydrochloride

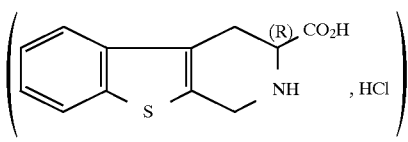

The expected product is obtained according to the process described in preparation A from β-3-benzo [b]thienyl-D-alanine.

Melting point: >260° C.

Preparation D: (3R)-1,2,3,4-Tetrahydrobenzo[b]isoquinoline-3-carboxylic Acid Hydrochloride

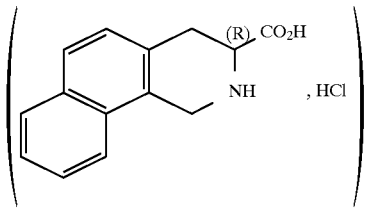

The expected product is obtained according to the process described in preparation A from β-2-naphthyl-D-alanine using concentrated hydrochloric acid instead of 1 N hydrochloric acid.

Melting point: >260° C.

Preparation E: (3R)-1,2,3,4-Tetrahydrobenzo[f]isoquinoline-3-carboxylic Acid Hydrochloride

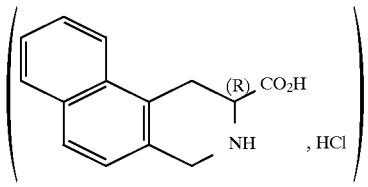

The expected product is obtained according to the process described in preparation A from β-1-naphthyl-D-alanine using concentrated hydrochloric acid instead of 1N hydrochloric acid.

Melting point: 174° C.

Preparations F and G:

Preparation F: (3R)-1,2,3,4-Tetrahydro-1-heptyl-β-carboline-3-carboxylic Acid, α Isomer

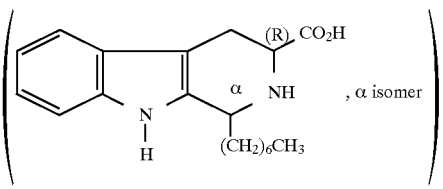

Preparation G: (3R)-1,2,3,4-Tetrahydro-1-heptyl-β-carboline-3-carboxylic Acid, β Isomer

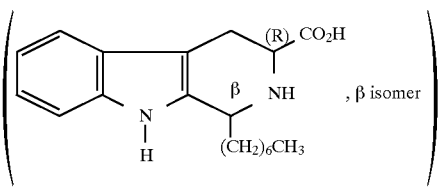

A mixture containing 147 mmol of D-tryptophan, 294 ml of 1 N sulfuric acid, 300 ml of ethanol and 294 mmol of octanal is stirred at 45° C. for 72 hours. The solution is concentrated and the residue is taken up in a water/methanol/ammonium hydroxide mixture. The methanol is evaporated at 45° C. and the precipitate is filtered off, washed with water and dried. The solid obtained is solubilized at high temperature in methanol. After cooling, the compound of preparation F crystallizes. It is then filtered and dried.

Preparation F: Melting point: 206° C.

The filtration liquor is then concentrated at 45° C. and the residue obtained is purified by chromatography on silica gel using, as eluent, a dichloromethane/methanol/acetic acid (90/10/1) mixture. The compound of preparation G is then obtained.

Preparation G: Melting point: 170° C.

Preparation H: (3S)-1,2,3,4-Tetrahydro-β-carboline-3-carboxylic Acid

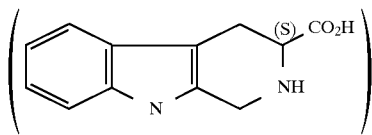

The expected product is synthesized according to the process described in preparation B and from (L)-tryptophan.

Preparation I: (6R)-1-Methyl-4,5,6,7-tetrahydroimidazo[4,5-c]pyridine-6-carboxylic Acid

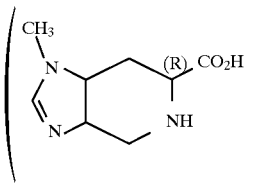

The expected product is synthesized according to the process described in preparation A from (D)-($N^\pi$-methyl) histidine.

Preparation J: (6R)-3-Methyl-4,5,6,7-tetrahydroimidazo[4,5-c]pyridine-6-carboxylic Acid The expected product is obtained according to the process described in preparation A from (D)-(Nᵗ-methyl)histidine.

Preparation K: (5R)-4,5,6,7-Tetrahydrothieno[2,3-c]pyridine-5-carboxylic Acid Hydrochloride

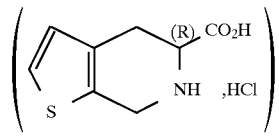

The expected product is prepared according to the process described in preparation A from β-3-thienylalanine synthesized according to the method described by M.S. Allen (Synth. Comm., 22 (14), 2077–2102, 1992).

Preparation L: (5R)-4,5,6,7-Tetrahydrofuro[2,3-c]pyridine-5-carboxylic Acid Hydrochloride

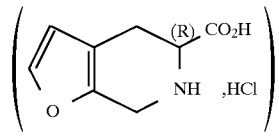

The expected product is prepared according to the process described in preparation A from β-3-furoalanine synthesized according to the method described by M.S. Allen (Synth. Comm., 22 (14), 2077–2102, 1992).

EXAMPLE 1

(6R)-5-(4-Methoxybenzenesulfonyl)-4,5,6,7-tetrahydrothieno[3,2-c]pyridine-6-(N-hydroxy)carboxamide Stage A: (6R)-5-(4-Methoxybenzenesulfonyl)-4,5,6,7-tetrahydrothieno[3,2-c]pyridine-6-carboxylic acid A mixture containing 36 mmol of the compound described in preparation A, 54 mmol of triethylamine, 43 mmol of 4-methoxybenzenesulfonic acid chloride in 100 ml of dioxane and 80 ml of water, is stirred overnight at 20° C. The mixture is then poured into 500 ml of ice-cold water and 500 ml of 4 N hydrochloric acid. After stirring for 15 minutes, the precipitate is filtered, rinsed with water, dried and gives the expected product.

Melting point: 110° C.

Stage B: (6R)-5-(4-Methoxybenzenesulfonyl)-4,5,6,7-tetrahydrothieno[3,2-c]pyridine-6-(N-allyloxy)carboxamide 10 mmol of the compound obtained in the preceding stage, 30 mmol of O-allylhydroxylamine hydrochloride, 17 ml of diisopropylethylamine, 10 mmol of hydroxybenzotriazole and 12 mmol of O-(benzotriazol-1-yl)-N,N,N',N'-tetramethyluronium tetrafluoroborate (TBTU) are stirred for 5 hours at 20° C. The mixture is then washed with water, with hydrochloric acid and then with a saturated aqueous sodium hydrogen carbonate solution. After drying and then evaporation, the residue is taken up and then purified by chromatography on silica gel using, as eluent, a dichloromethane/ethyl acetate (95/5, then 70/30) mixture. After drying and evaporation, the expected product is obtained.

Stage C: (6R)-5-(4-Methoxybenzenesulfonyl)-4,5,6,7-tetrahydrothieno[3,2-c]pyridine-6-(N-hydroxy)carboxamide 3.9 mmol of the compound obtained in the preceding stage, 140 mg of $(Ph_3P)_2PdCl_2$ and 0.7 ml of acetic acid in 50 ml of dichloromethane are stirred for 10 minutes at 20° C. 2.2 ml of tributyltin hydride are then added and the whole is kept stirring for 15 minutes at 20° C. The reaction medium is then washed with water and then the solvent is evaporated. The residue is taken up in dichloromethane. The organic phase is washed with 1 N hydrochloric acid and then with a saturated sodium hydrogen carbonate solution. After drying and evaporation, the residue is purified by chromatography on silica gel using, as eluent, a dichloromethane/methanol (95/5) mixture. The expected product is then obtained.

| Elemental microanalysis: | | | | |
|---|---|---|---|---|
| | C % | H % | N % | S % |
| Calculated | 48.90 | 4.38 | 7.60 | 17.41 |
| Found | 49.84 | 4.49 | 7.23 | 16.64 |

Mass spectrum: FAB $[M+H]^+$: m/z=369

EXAMPLE 2

(3R)-2-(4-Methoxybenzenesulfonyl)-1,2,3,4-tetrahydro-β-carboline-3-(N-hydroxy)carboxamide Stage A: (3R)-2-(4-Methoxybenzenesulfonyl)-1,2,3,4-tetrahydro-β-carboline-3-carboxylic acid The expected product is obtained according to the process described in stage A of Example 1 using, as starting material, the compound described in preparation B.

Melting point: 154° C.

Stage B: (3R)-2-(4-Methoxybenzenesulfonyl)-1,2,3,4-tetrahydro-β-carboline-3-(N-allyloxy)carboxamide The expected product is obtained according to the process described in Stage B of Example 1 from the compound described in the preceding stage.

Stage C: (3R)-2-(4-Methoxybenzenesulfonyl)-1,2,3,4-tetrahydro-β-carboline-3-(N-hydroxy)carboxamide The expected product is obtained according to the process described in Stage C of Example 1 using the compound described in the preceding stage.

Melting point: 122° C.

| Elemental microanalysis: | | | | |
|---|---|---|---|---|
| | C % | H % | N % | S % |
| Calculated | 56.84 | 4.78 | 10.47 | 7.99 |
| Found | 56.40 | 4.56 | 10.34 | 8.25 |

EXAMPLE 3

(3R)-2-(4-Methoxybenzenesulfonyl)-1,2,3,4-tetrahydrobenzo[b]thieno[2,3-c]pyridine-3-(N-hydroxy)carboxamide, Sodium Salt The expected product is obtained according to the process described in Example 1 using, in Stage A, the product described in preparation C.

Stage A: (3R)-2-(4-Methoxybenzenesulfonyl)-1,2,3,4-tetrahydrobenzo[b]thieno[2,3-c]pyridinecarboxylic acid Stage B: (3R)-2-(4-Methoxybenzenesulfonyl)-1,2,3,4-tetrahydrobenzo[b]thieno[2,3-c]pyridine-3-(N-allyloxy)carboxamide Stage C: (3R)-2-(4-Methoxybenzenesulfonyl)-1,2,3,4-tetrahydrobenzo[b]thieno[2,3-c]pyridine-3-(N-hydroxy)carboxamide, sodium salt

EXAMPLE 4

(3R)-2-(4-Methoxybenzenesulfonyl)-1,2,3,4-tetrahydrobenzo[h]-isoquinoline-3-(N-hydroxy)carboxamide The expected product is obtained according to the process described in Example 1 using, in Stage A, the product described in preparation D.
Stage A: (3R)-2-(4-Methoxybenzenesulfonyl)-1,2,3,4-tetrahydrobenzo[h]isoquinoline-3-carboxylic acid
Stage B: (3R)-2-(4-Methoxybenzenesulfonyl)-1,2,3,4-tetrahydrobenzo[h]isoquinoline-3-(N-allyloxy)carboxamide
Stage C: (3R)-2-(4-Methoxybenzenesulfonyl)-1,2,3,4-tetrahydrobenzo[h]isoquinoline-3-(N-hydroxy)carboxamide Mass spectrum: FAB [M+H]$^+$: m/z=413

EXAMPLE 5

(3R)-2-(4-Methoxybenzenesulfonyl)-1,2,3,4-tetrahydrobenzo[f]-isoquinoline-3-(N-hydroxy)carboxamide Stage A: (3R)-2-(4-Methoxybenzenesulfonyl)-1,2,3,4-tetrahydrobenzo[f]-isoquinoline-3-carboxylic acid
Stage B: (3R)-2-(4-Methoxybenzenesulfonyl)-1,2,3,4-tetrahydrobenzo[f]-isoquinoline-3-(N-allyloxy)carboxamide
Stage C: (3R)-2-(4-Methoxybenzenesulfonyl)-1,2,3,4-tetrahydrobenzo[f]-isoquinoline-3-(N-hydroxy)carboxamide Mass spectrum: FAB [M+H]$^+$: m/z=413

EXAMPLE 6

(3R)-2-(4-Methoxybenzenesulfonyl)-1,2,3,4-tetrahydro-1-heptyl-β-carboline-3-(N-hydroxy)carboxamide, α Isomer The expected product is obtained according to the process described in Example 1 using, in Stage A, the product described in preparation F.
Stage A: (3R)-2-(4-Methoxybenzenesulfonyl)-1,2,3,4-tetrahydro-1-heptyl-β-carboline-3-carboxylic acid, α isomer
Stage B: (3R)-2-(4-Methoxybenzenesulfonyl)-1,2,3,4-tetrahydro-1-heptyl-β-carboline-3-(N-allyloxy)carboxamide, α isomer
Stage C: (3R)-2-(4-Methoxybenzenesulfonyl)-1,2,3,4-tetrahydro-1-heptyl-β-carboline-3-(N-hydroxy)carboxamide, α isomer Mass spectrum: FAB [M+H]$^+$: m/z=500

EXAMPLE 7

(3R)-2-(4-Methoxybenzenesulfonyl)-1,2,3,4-tetrahydro-1-heptyl-β-carboline-3-(N-hydroxy)carboxamide, β Isomer The expected product is obtained according to the process described in Example 1 using, in Stage A, the product described in preparation G.
Stage A: (3R)-2-(4-Methoxybenzenesulfonyl)-1,2,3,4-tetrahydro-1-heptyl-β-carboline-3-carboxylic acid, β isomer
Stage B: (3R)-2-(4-Methoxybenzenesulfonyl)-1,2,3,4-tetrahydro-1-heptyl-β-carboline-3-(N-allyloxy)carboxamide, β isomer
Stage C: (3R)-2-(4-Methoxybenzenesulfonyl)-1,2,3,4-tetrahydro-1-heptyl-β-carboline-3-(N-hydroxy)carboxamide, β isomer Mass spectrum: FAB [M+H]$^+$: m/z=500

EXAMPLE 8

(3S)-2-(4-Methoxybenzenesulfonyl)-1,2,3,4-tetrahydro-β-carboline-3-(N-hydroxy)carboxamide The expected product is obtained according to the process described in Example 1 using, in Stage A, the product described in preparation H.
Stage A: (3S)-2-(4-Methoxybenzenesulfonyl)-1,2,3,4-tetrahydro-β-carboline-3-carboxylic acid
Melting point: 230° C.
Stage B: (3S)-2-(4-Methoxybenzenesulfonyl)-1,2,3,4-tetrahydro-β-carboline-3-(N-benzyloxy)carboxamide
At this stage, O-allylhydroxylamine is replaced with O-benzylhydroxylamine.
Stage C: (3S)-2-(4-Methoxybenzenesulfonyl)-1,2,3,4-tetrahydro-β-carboline-3-(N-hydroxy)carboxamide Mass spectrum: FAB [M+H]$^+$: m/z=402

EXAMPLE 9

(2R)-1-(4-Methoxyphenylsulfonyl)indoline-2-(N-hydroxy)carboxamide

The expected product is obtained according to the process described in Example 1 using, in Stage A, (2R)-indoline-2-carboxylic acid.
Stage A: (2R)-1-(4-Methoxyphenylsulfonyl)indoline-2-carboxylic acid
Stage B: (2R)-1-(4-Methoxyphenylsulfonyl)indoline-2-(N-benzyloxy)carboxamide
At this stage, O-allylhydroxylamine is replaced with O-benzylhydroxylamine.
Stage C: (2R)-1-(4-Methoxyphenylsulfonyl)indoline-2-(N-hydroxy)carboxamide
At this stage, the deprotection is carried out in methanol, at atmospheric pressure using Pd(OH)$_2$ as catalyst.

Elemental microanalysis:

|  | C % | H % | N % | S % |
|---|---|---|---|---|
| Calculated | 55.16 | 4.63 | 8.04 | 9.20 |
| Found | 55.25 | 4.87 | 7.85 | 8.52 |

EXAMPLE 10

(3R)-2-(4-Methoxybenzoyl)-1,2,3,4-tetrahydroisoquinoline-3-(N-hydroxy)carboxamide Stage A: (3R)-2-(4-Methoxybenzoyl)-1,2,3,4-tetrahydroisoquinoline-3-carboxylic acid
The expected product is obtained according to the process described in stage A of Example 1 from (3R)-1,2,3,4-tetrahydroisoquinoline-3-carboxylic acid and (4-methoxy)benzoyl chloride.
Melting point 198° C.
Stage B: (3R)-2-(4-Methoxybenzoyl)-1,2,3,4-tetrahydroisoquinoline-3-(N-benzyloxy)carboxamide
The expected product is obtained according to the process described in Stage B of Example 1 from the compound described in the preceding stage and O-benzylhydroxylamine.
Stage C: (3R)-2-(4-Methoxybenzoyl)-1,2,3,4-tetrahydroisoquinoline-3-(N-hydroxy)carboxamide (Melting point: =118° C.
Mass spectrum: FAB [M+Na$^+$]=441

Mass spectrum: FAB [M+H]$^+$: m/z=500)

The expected product is obtained according to the process described in Stage C of Example 1 from the compound described in the preceding stage.

Elemental microanalysis:

|            | C %   | H %  | N %  |
|------------|-------|------|------|
| Calculated | 66.25 | 5.56 | 8.75 |
| Found      | 66.10 | 5.64 | 8.58 |

EXAMPLE 11

(6R)-1-Methyl-5-(4-methoxybenzenesulfonyl)-4,5,6,7-tetrahydro-imidazo[4,5-c]pyridine-6-(N-hydroxy)carboxamide Hydrochloride The expected product is obtained according to the process described in Example 1 using, in Stage A, the product described in preparation I.

Stage A: (6R)-1-Methyl-5-(4-methoxybenzenesulfonyl)-4,5,6,7-tetrahydroimidazo[4,5-c]pyridine-6-carboxylic acid Stage B: (6R)-1-Methyl-5-(4-methoxybenzenesulfonyl)-4,5,6,7-tetrahydroimidazo[4,5-c]pyridine-6-(N-allyloxy)carboxamide Stage C: (6R)-1-Methyl-5-(4-methoxybenzenesulfonyl)-4,5,6,7-tetrahydroimidazo[4,5-c]pyridine-6-(N-hydroxy)carboxamide hydrochloride Elemental microanalysis:

|            | C %   | H %  | N %   | Cl % | S %  |
|------------|-------|------|-------|------|------|
| Calculated | 44.72 | 4.75 | 13.91 | 8.80 | 7.96 |
| Found      | 44.78 | 4.69 | 13.72 | 8.84 | 7.95 |

EXAMPLE 12

(6R)-3-Methyl-5-(4-methoxybenzenesulfonyl)-4,5,6,7-tetrahydroimidazo-[4,5-c]pyridine-6-(N-hydroxy)carboxamide Hydrochloride The expected product is obtained according to the process described in Example 1 using, in Stage A, the product described in the preparation J.

Stage A: (6R)-3-Methyl-5-(4-methoxybenzenesulfonyl)-4,5,6,7-tetrahydroimidazo[4,5-c]pyridine-6-carboxylic acid Stage B: (6R)-3-Methyl-5-(4-methoxybenzenesulfonyl)-4,5,6,7-tetrahydroimidazo[4,5-c]pyridine-6-(N-allyloxy)carboxamide Stage C: (6R)-3-Methyl-5-(4-methoxybenzenesulfonyl)-4,5,6,7-tetrahydroimidazo[4,5-c]pyridine-6-(N-hydroxy)carboxamide hydrochloride Elemental microanalysis:

|            | C %   | H %  | N %   | Cl % | S %  |
|------------|-------|------|-------|------|------|
| Calculated | 44.72 | 4.75 | 13.91 | 8.80 | 7.96 |
| Found      | 44.77 | 4.70 | 13.80 | 9.11 | 8.10 |

EXAMPLE 13

(3R)-2-[(3-Phenyl)propylsulfonyl]-1,2,3,4-tetrahydroisoquinoline-3-(N-hydroxy)carboxamide The expected product is obtained according to the process described in Example 10 using, in Stage A, 3-phenylpropylsulfonyl chloride.

Stage A: (3R)-2-[(3-Phenyl)propylsulfonyl]-1,2,3,4-tetrahydroisoquinoline-3-carboxylic acid Stage B: (3R)-2-[(3-Phenyl)propylsulfonyl]-1,2,3,4-tetrahydroisoquinoline-3-(N-benzyloxy)carboxamide Stage C: (3R)-2-[(3-Phenyl)propylsulfonyl]-1,2,3,4-tetrahydroisoquinoline-3-(N-hydroxy)carboxamide Elemental microanalysis:

|            | C %   | H %  | N %  | S %  |
|------------|-------|------|------|------|
| Calculated | 60.94 | 5.92 | 7.48 | 8.56 |
| Found      | 60.67 | 5.91 | 7.58 | 8.36 |

EXAMPLE 14

(3R)-2-[(4-Methoxybenzene)aminosulfonyl]-1,2,3,4-tetrahydro-isoquinoline-3-(N-hydroxy)carboxamide The expected product is obtained according to the process described in Example 10 using, in Stage A, 4-methoxybenzeneaminosulfonyl chloride.

Stage A: (3R)-2-[(4-Methoxybenzene)aminosulfonyl-1,2,3,4-tetrahydroisoquinoline-3-carboxylic acid Stage B: (3R)-2-[(4-Methoxybenzene)aminosulfonyl]-1,2,3,4-tetrahydroisoquinoline-3-(N-benzyloxy)carboxamide Stage C: (3R)-2-[(4-Methoxybenzene)aminosulfonyl]-1,2,3,4-tetrahydroisoquinoline-3-(N-hydroxy)carboxamide Elemental microanalysis:

|            | C %   | H %  | N %   | S %  |
|------------|-------|------|-------|------|
| Calculated | 54.10 | 5.07 | 11.13 | 8.50 |
| Found      | 54.13 | 5.15 | 10.92 | 8.16 |

EXAMPLE 15

(5R)-6-(4-Methoxybenzenesulfonyl)-4,5,6,7-tetrahydro-thieno[2,3-c]pyridine-5-(N-hydroxy)carboxamide The expected product is obtained according to the process described in Example 1, from the compound described in preparation K.

Elemental microanalysis:

|            | C %   | H %  | N %  | S %   |
|------------|-------|------|------|-------|
| Calculated | 48.90 | 4.38 | 7.60 | 17.41 |
| Found      | 49.08 | 4.66 | 7.43 | 17.19 |

EXAMPLE 16

(5R)-6-(4-Trifluoromethoxybenzenesulfonyl)-4,5,6,7-tetrahydro-thieno[2,3-c]pyridine-5-(N-hydroxy)carboxamide The expected product is obtained according to the process described in Example 1, from the compound described in preparation K and 4-trifluoromethoxybenzenesulfonyl chloride.

Melting point: 136°–138° C.

| Elemental microanalysis: | | | | |
|---|---|---|---|---|
| | C % | H % | N % | S % |
| Calculated | 42.65 | 3.10 | 6.63 | 15.18 |
| Found | 42.63 | 3.30 | 6.51 | 15.04 |

EXAMPLE 17

(6R)-5-(4-Phenylbenzenesulfonyl)-4,5,6, 7-tetrahydrothieno[3,2-c]pyridine-6-(N-hydroxy)carboxamide The expected product is obtained according to the process described in Example 1, from the compound described in preparation A and 4-phenylbenzenesulfonic acid chloride.

| Elemental microanalysis: | | | | |
|---|---|---|---|---|
| | C % | H % | N % | S % |
| Calculated | 57.95 | 4.38 | 6.76 | 15.47 |
| Found | 57.61 | 4.77 | 6.42 | 15.22 |

EXAMPLE 18

(6R)-5-(4-Trifluoromethoxybenzenesulfonyl)-4,5,6, 7-tetrahydro-thieno[3,2-c]pyridine-6-(N-hydroxy)carboxamide The expected product is obtained according to the process described in Example 1, from the compound described in preparation A and 4-trifluoromethoxybenzenesulfonic acid chloride.

Mass spectrum: FAB$^+$: [M+H]$^+$: m/z=423

EXAMPLE 19

(6R)-5-[(2-Naphthyl)sulfonyl]-4,5,6, 7-tetrahydrothieno[3,2-c]pyridine-6-(N-hydroxy)carboxamide The expected product is obtained according to the process described in Example 1, from the compound described in preparation A and 2-naphthalenesulfonic acid chloride.

Mass Spectrum: FAB$^+$: [M+H]+: m/z=389

EXAMPLE 20

(3R)-2-(4-Methoxybenzenesulfonyl)-1,2,3,4-tetrahydro-benzo[b]thieno[2,3-c]pyridine-3-(N-methoxy)carboxamide The expected product is obtained by reacting the compound described in Stage A of Example 3 with N-methoxylamine in the presence of the coupling reagent DCC-HOBT.

Melting point: 202° C.

| Elemental microanalysis: | | | | |
|---|---|---|---|---|
| | C % | H % | N % | S % |
| Calculated | 55.52 | 4.66 | 6.48 | 14.83 |
| Found | 55.89 | 4.78 | 6.47 | 15.05 |

EXAMPLE 21

(3R)-2-(4-Methoxybenzenesulfonyl)-1,2,3,4-tetrahydrobenzo-[b]thieno[2,3-c]pyridine-3-(N-hydroxy-N-methyl)carboxamide The expected product is obtained by reacting the compound described in stage A of Example 3 with (N-methyl)hydroxylamine in the presence of the coupling reagent DCC-HOBT.

Melting point: 224° C.

| Elemental microanalysis: | | | | |
|---|---|---|---|---|
| | C % | H % | N % | S % |
| Calculated | 55.54 | 4.66 | 6.48 | 14.83 |
| Found | 55.86 | 4.78 | 6.39 | 14.60 |

EXAMPLE 22

(3R)-2-(4-Methoxybenzenesulfonyl)-1,2,3,4-tetrahydrobenzo-[b]thieno[2,3-c]pyridine-3-(N-methoxy-N-methyl)carboxamide The expected product is obtained by reacting the compound described in Stage A of Example 3 with N-methoxy-N-methylamine in the presence of the coupling reagent HOBT-TBTU.

| Elemental microanalysis: | | | | |
|---|---|---|---|---|
| | C % | H % | N % | S % |
| Calculated | 56.49 | 4.97 | 6.27 | 14.36 |
| Found | 56.47 | 5.09 | 6.32 | 14.06 |

EXAMPLE 23

(6R)-5-(4-Methoxybenzenesulfonyl)-4,5,6,7-tetrahydro-imidazo[4,5-c]pyridine-6-(N-hydroxy)carboxamide Hydrochloride The expected product is obtained according to the process described in Example 1, from Spinacin, and converted to the corresponding hydrochloride.

| Elemental microanalysis: | | | | | |
|---|---|---|---|---|---|
| | C % | H % | N % | Cl % | S % |
| Calculated | 43.25 | 4.41 | 14.41 | 9.12 | 8.25 |
| Found | 42.91 | 4.52 | 13.85 | 9.55 | 8.02 |

EXAMPLE 24

(3R)-2-(4-Methoxybenzenesulfonyl)-9-methyl-1,2,3,4-tetrahydro-β-carboline-3-(N-hydroxy)carboxamide The expected product is obtained according to the process described in Example 1, from (3R)-9-methyl-1,2,3,4-tetrahydro-β-carboline-3-carboxylic acid.

Melting point: 214° C.

| Elemental microanalysis: | | | | |
|---|---|---|---|---|
| | C % | H % | N % | S % |
| Calculated | 57.82 | 5.09 | 10.11 | 7.72 |
| Found | 57.35 | 5.28 | 9.57 | 7.74 |

EXAMPLE 25

(3R)-2-(4-Methoxybenzenesulfonyl)-9-benzyl-1,2,3,4-tetrahydro-β-carboline-3-(N-hydroxy)carboxamide The expected product is obtained according to the process described in Example 1, from (3R)-9-benzyl-1,2,3,4-tetrahydro-β-carboline-3-carboxylic acid.

| Elemental microanalysis: | | | | |
|---|---|---|---|---|
| | C % | H % | N % | S % |
| Calculated | 63.53 | 5.13 | 8.55 | 6.52 |
| Found | 63.24 | 5.12 | 8.34 | 6.13 |

EXAMPLE 26

(3R)-2-(4-Phenylbenzenesulfonyl)-9-benzyl-1,2,3,4-tetrahydro-β-carboline-3-(N-hydroxy)carboxamide The expected product is obtained according to the process described in Example 1, from (3R)-9-benzyl-1,2,3,4-tetrahydro-β-carboline-3-carboxylic acid and 4-phenylbenzenesulfonyl chloride.

Mass spectrum: FAB+: [M+H]+: m/z=538

EXAMPLE 27

(3R)-2-(4-Pentylbenzenesulfonyl)-9-benzyl-1,2,3,4tetrahydro-β-carboline-3-(N-hydroxy)carboxamide The expected product is obtained according to the process described in Example 1, from (3R)-9-benzyl-1,2,3,4-tetrahydro-β-carbolinecarboxylic acid and 4-pentylbenzenesulfonic acid.

Melting point: 94° C.

| Elemental microanalysis: | | | | |
|---|---|---|---|---|
| | C % | H % | N % | S % |
| Calculated | 67.77 | 6.26 | 7.90 | 6.03 |
| Found | 67.96 | 6.29 | 7.62 | 5.92 |

EXAMPLE 28

(5R)-6-(4-Methoxybenzenesulfonyl)-4,5,6,7-tetrahydrofuro[2,3-c]pyridine-5-(N-hydroxy)carboxamide The expected product is obtained according to the process described in Example 1, from the compound described in preparation L.

Melting point: 149° C.

| Elemental microanalysis: | | | | |
|---|---|---|---|---|
| | C % | H % | N % | S % |
| Calculated | 51.13 | 4.58 | 7.95 | 9.10 |
| Found | 51.18 | 4.60 | 7.77 | 9.11 |

EXAMPLE 29

(3R)-2-(4-Methoxybenzenesulfonyl)-1,2,3,4tetrahydroisoquinoline-3-carbohydroximamide Stage A: (3R)-2-(4-Methoxybenzenesulfonyl)-1,2,3,4-tetrahydroisoquinoline-3-carboxylic acid The expected product is obtained according to the process described in Stage A of Example 1, from (3R)-1,2,3,4-tetrahydroisoquinoline-3-carboxylic acid and 4-methoxybenzenesulfonyl chloride.

Stage B: (3R)-2-(4-Methoxybenzenesulfonyl)-1,2,3,4-tetrahydroisoquinoline-3-carboxamide The expected product is obtained by reacting the compound described in the preceding stage with ethyl chloroformate in tetrahydrofuran/triethylamine medium and then with ammonium hydroxide.

Stage C: (3R)-2-(4-Methoxybenzenesulfonyl)-3-cyano-1,2,3,4-tetrahydroisoquinoline The expected product is obtained by reacting the compound described in the preceding stage in pyridine in the presence of POCl₃.

Stage D: (3R)-2-(4-Methoxybenzenesulfonyl)-1,2,3,4-tetrahydroisoquinoline-3-carbohydroximamide The expected product is obtained by reacting the compound described in the preceding stage with hydroxylamine.

| Elemental microanalysis: | | | | |
|---|---|---|---|---|
| | C % | H % | N % | S % |
| Calculated | 56.50 | 5.30 | 11.63 | 8.87 |
| Found | 56.57 | 5.38 | 11.03 | 8.95 |

EXAMPLE 30

(6R)-2-(4-Trifluoromethoxybenzenesulfonyl)-4,5,6,7-tetrahydro-thieno[3,2-c]pyridine-6-(N-hydroxy-N-methyl)carboxamide The expected product is obtained according to the process described in Example 21, from the compound described in Stage A of Example 1.

| Elemental microanalysis: | | | | |
|---|---|---|---|---|
| | C % | H % | N % | S % |
| Calculated | 44.03 | 3.46 | 6.42 | 14.69 |
| Found | 44.02 | 3.13 | 6.39 | 14.80 |

EXAMPLE 31

(6R)-5-(4-Methoxybenzenesulfonyl)-7-hydroxy-4,5,6,7-tetrahydro-thieno[3,2-c]pyridine-6-(N-hydroxy)carboxamide The expected product is obtained according to the process described in Example 1, from (6R)-7-hydroxy-4,5,6,7-tetrahydrothieno[3,2-c]pyridine-6-carboxylic acid.

EXAMPLE 32

(6R)-1-Methyl-5-(4-methoxybenzenesulfonyl)-4,5,6,
7-tetrahydropyrrolo-[3,2-c]pyridine-6-(N-hydroxy)
carboxamide The expected product is obtained according to the process described in Example 1, from 1-methyl-4,5,6,7-tetrahydropyrrolo[3,2-c]pyridine-6-carboxylic acid.

EXAMPLE 33

(5R)-6-(4-Methoxybenzenesulfonyl)-4,5,6,7-
tetrahydropyrrolo[2,3-c]pyridine-5-(N-hydroxy)
carboxamide The expected product is obtained according to the process described in Example 1, from (5R)-4,5,6,7-tetrahydropyrrolo[2,3-c]pyridine-5-carboxylic acid.

EXAMPLE 34

(7R)-6-(4-Methoxybenzenesulfonyl)-5,6,7,8-
tetrahydropyrido[3,2-c]pyridine-7-(N-hydroxy)
carboxamide The expected product is obtained according to the process described in Example 1, from (7R)-5,6,7,8-tetrahydropyrido[3,2-c]pyridine-7-carboxylic acid.

EXAMPLE 35

(6R)-7-(4-Methoxybenzenesulfonyl)-5,6,7,8-
tetrahydropyrido[2,3-c]pyridine-6-(N-hydroxy)
carboxamide The expected product is obtained according to the process described in Example 1, from (7R)-5,6,7,8-tetrahydropyrido[2,3-c]pyridine-7-carboxylic acid.

EXAMPLE 36

(6R)-5-(4-Trifluoromethoxyphenylsulfonyl)-4,5,6,7-
tetrahydroimidazo-[4,5-c]pyridine-6-(N-hydroxy)
carboxamide The expected product is obtained according to the process described in Example 1, from Spinacin and 4-trifluoromethoxyphenylsulfonyl chloride.

EXAMPLE 37

(6R)-5-(4-Phenylbenzenesulfonyl)-4,5,6,7-
tetrahydroimidazo[4,5-c]pyridine-6-(N-hydroxy)
carboxamide The expected product is obtained according to the process described in Example 1, from Spinacin and 4-phenylbenzenesulfonyl chloride.

EXAMPLE 38

(5R)-6-(4-rifluoromethoxybenzenesulfonyl)-4,5,6,7-
tetrahydrofuro[2,3-c]pyridine-5-(N-hydroxy)
carboxamide The expected product is obtained according to the process described in Example 1, using the compound described in preparation L as starting material.

EXAMPLE 39

(SR)-6-(4-Phénylbenzenesulfonyl)-4,5,6,7-
tétrahydrofuro[2,3-c]pyridine-5-(N-hydroxy)
carboxamide The expected product is obtained according to the process described in Example 1, using the compound described in preparation L as starting material.

EXAMPLE 40

(5R)-6-(4-Pyridylsulfonyl)-4,5,6,7-tétrahydrofuro[2,
3-c]pyridine-5-(N-hydroxy)carboxamide The expected product is obtained according to the process described in Example 1, using the compound described in preparation L as starting material.

EXAMPLE 41

(5R)-6-(3-Pyridylsulfonyl)-4,5,6,7-tétrahydrofuro[2,
3-c]pyridine-5-(N-hydroxy)carboxamide The expected product is obtained according to the process described in Example 1, using the compound described in preparation L as starting material.

EXAMPLE 42

(5R)-6-[4-(Pyridin-4-yl)phénylsulfonyl]-4,5,6,7-
tétrahydrofuro[2,3-c]pyridine-5-(N-hydroxy)
carboxamide The expected product is obtained according to the process described in Example 1, using the compound described in preparation L as starting material.

EXAMPLE 43

(5R)-6-{4-[2-(Diméthylamino)éthoxy]
phénylsulfonyl}-4,5,6,7-tétrahydrofuro[2,3-c]
pyridine-5-(N-hydroxy)carboxamide The expected product is obtained according to the process described in Example 1, using the compound described in preparation L as starting material.

EXAMPLE 44

(5R)-6-{4-(Pyrimidin-2-yl)phénylsulfonyl]-4,5,6,7-
tétrahydrofuro[2,3-c]pyridine-5-(N-hydroxy)
carboxamide The expected product is obtained according to the process described in Example 1, using the compound described in preparation L as starting material.

EXAMPLE 45

(5R)-6-{4-(Pyrimidin-5-yl)phénylsulfonyl]-4,5,6,7-
tétrahydrofuro[2,3-c]pyridine-5-(N-hydroxy)
carboxamide The expected product is obtained according to the process described in Example 1, using the compound described in preparation L as starting material.

EXAMPLE 46

(6R)-5-[4-(4-Fluorophényl)benzènesulfonyl]-4,5,6,
7-tétrahydroimidazo [4,5-c]pyridine-6-(N-hydroxy)
carboxamide The expected product is obtained according to the process described in Example 1, using the Spinacine as starting material.

EXAMPLE 47

(6R)-5-[4-(Pyridin-4-yl)phénylsulfonyl]-4,5,6,7-
tétrahydroimidazo[4,5-c]pyridine-6-(N-hydroxy)
carboxamide The expected product is obtained according to the process described in Example 1, using the Spinacine as starting material.

EXAMPLE 48

(6R)-5-(4-Pyridylsulfonyl)-4,5,6,7-tétrahydroimidazo[4,5-c]pyridine-6-(N-hydroxy)carboxamide Le produit attendu est obtenu selon le procédé décrit dans l'exemple 1 à partir de la Spinacine.

EXAMPLE 49

(6R)-5-(3-Pyridylsulfonyl)-4,5,6,7-tétrahydroimidazo[4,5-c]pyridine-6-(N-hydroxy)carboxamide The expected product is obtained according to the process described in Example 1, using the Spinacine as starting material.

Pharmacological Study of the Derivatives of the Invention

EXAMPLE 50

Enzymatic inhibition of metalloproteases

The four human recombinant enzymes MMP-1 (interstitial collagenase), MMP-2 (gelatinase A of 72 kDa), MMP-3 (stromelysine 1) and MMP-9 (gelatinase B of 92 kDa) are activated with APMA (4-aminophenylmercuric acetate). The enzymatic tests are carried out with a peptide-like substrate:

DnpProChaGlyCys(Me)HisAlaLys(Nma)NH$_2$, cleaved between the Glycine and the Cysteine so as to produce a fluorescent derivative described by D. M. Bickett et al. (Anal. Biochem., 212, 58–64, 1993).

The reactions, carried out in a 50 mM Tris buffer containing 200 mM NaCl, 5 mM CaCl$_2$, 0.1% Brij 35 at pH 7.7, are initiated with 20 $\mu$M of substrate in a total volume of 100 $\mu$l at 37° C.

The fluorescence obtained after six hours is read on a 96-well plate in a fluorimeter equipped with a combination of filters of 340 nm and 440 nm for the excitation and the emission. During this test, most of the compounds of the invention exhibited IC$_{50}$ values of between 10 and 500 nM for the enzyme MMP-1, between 0.01 and 50 nM for the enzymes MMP-2, MMP-3 and MMP-9.

EXAMPLE 51

Degradation of the Cartilaginous Matrix In Vivo

The compounds of the invention were studied in a model of destruction of the cartilaginous matrix induced by IL-1$\beta$. The trials carried out on guinea pig cartilage relate:
- on the one hand, to the degradation of collagen: colorimetric assay according to the Grant technique (Grant R. A. Estimation of OH-proline by the autoanalyser, J. Clin. Path. 1964, 17, 685) of the OH-proline fraction released by the tissue brought into contact, for 3 days, with IL-1$\beta$ (10 mg/ml) and of plasminogen (30 $\mu$g/ml),
- on the other hand, to the degradation of proteoglycans: radioisotopic measurement of the glycosaminoglycan fraction released by the tissue during the 3 days of contact with IL-1$\beta$ (10 mg/mil), the cartilage having been labeled beforehand with $^{35}$SO$_4$.

The compounds of the invention were studied by addition to the culture medium for the 3 days of assay. For concentrations of between 10$^{-7}$ and 10$^{-4}$M, they strongly blocked the degradation of collagen and the proteoglycans. By way of example, the activities exerted by some compounds of the invention are the following:

|  | collagen | proteoglycans |
|---|---|---|
|  | % protection at 10$^{-6}$M | % protection at 3 × 10$^{-5M}$ |
| Example 1 | 98% | 45% |
| Example 7 | 47% | 100% |
| Example 15 | 98% | 60% |
| Example 23 | 88% | 24% |
| Example 28 | 79% | 34% |

EXAMPLE 52

Angiogenesis In Vitro

Sections of thoracic aorta from 8- to 12-week old male Fischer 344 rats are immersed in a collagen type I gel according to the Nicosia and Ottinetti method (1990). After five days of culture in serum-free medium, the preparations are examined under a microscope and the formation of pseudovessels is quantified in terms of vascular density after digitization and image analysis.

By way of example, during this test, at 100 nM, the compound of Example 1 produced 87% inhibition and the compound of Example 28 produced 85% inhibition.

EXAMPLE 53

Invasion In Vitro

The tests of invasion are carried out according to the following procedure: murine Lewis carcinoma cells (LLC) are deposited on the top face of a Transwell filter coated with an artificial extracellular matrix and are cultured in medium with serum for 24 h. The cells are then exposed to the vital stain 3-[4,5-dimethylthiazol-2-yl]-2,5-diphenyltetrazolium bromide and they are removed from the top face of the filter. The formazan crystals present under the filter are solubilized in a concentrated mixture of sodium dodecyl sulfate and dimethylformamide. The absorption at 540 nm of the corresponding colored mixture is then used to indirectly quantify cellular invasion.

By way of example, during this test, at 1 $\mu$M, the compound of Example 1 produced 45% inhibition and the compound of Example 28 produced 44% inhibition.

EXAMPLE 54

Pharmaceutical Composition

Preparation formula for 1000 tablets containing 10-mg doses:

| | |
|---|---|
| Compound of Example 1 | 10 g |
| Hydroxypropylcellulose | 2 g |
| Wheat starch | 10 g |
| Lactose | 100 g |
| Magnesium stearate | 3 g |
| Talc | 3 g |

We claim:
1. A compound selected from those of formula (I):

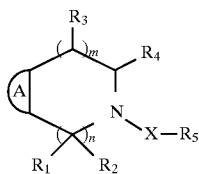

in which:

m and n, are both 1, $R_1$ and $R_2$, which are identical or different, represent hydrogen, linear or branched ($C_1$–$C_6$)alkyl optionally substituted with aryl, aryl, or $R_1$ and $R_2$ form with the carbon atom carrying them carbonyl, or ($C_3$–$C_7$) cycloalkyl, $R_3$ represents hydrogen, linear or branched ($C_1$–$C_6$)alkyl, hydroxyl, linear or branched ($C_1$–$C_6$)alkoxy, or aryl, $R_4$ represents any one of the following groups:

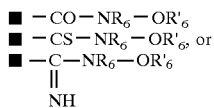

in which:

$R_6$ and $R'_6$, which are identical or different, represent hydrogen or linear or branched ($C_1$–$C_6$)alkyl,

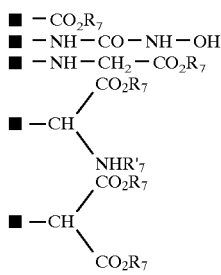

in which:

$R_7$ and $R'_7$, which are identical or different, represent hydrogen or linear or branched ($C_1$–$C_6$)alkyl optionally substituted with aryl, X represents —$SO_2$—, —CO—, or —$SO_2$NH—, $R_5$ represents:
  linear or branched ($C_1$–$C_6$)alkyl, optionally substituted with one or more halogen or hydroxyl, linear or branched ($C_1$–$C_6$)alkoxy, aryl, or —$CO_2R_7$ in which $R_7$ has the same meaning as above,
  ($C_3$–$C_7$)cycloalkyl,
  aryl,
  or a optionally substituted pyridinyl, A represents a 2,3 fused ring, its optical and stereo isomers and its addition salts with a pharmaceutically-acceptable acid or base.

2. A compound of claim 1, wherein $R_4$ represents —CO—$NR_6$—$OR'_6$.

3. A compound of claim 2, wherein $R_4$ represents —CO—NHOH.

4. A compound of claim 1, wherein X represents —$SO_2$—.

5. A compound wherein $R_5$ represents an optionally substituted aryl group.

6. A compound of claim 1, which is (5R)-6-(4-methoxybenzenesulfonyl)-4,5,6,7-tetrahydrofuro[2,3-c]pyridine-(5R)-(N-hydroxy)carboxamide.

7. A pharmaceutical composition useful as a metalloprotease inhibitor comprising as active principle an effective amount of a compound as claimed in claim 1, together with one or more pharmaceutically-acceptable excipients or vehicles.

8. A method for treating an animal or human living body afflicted with a disease selected from arthrosis and metastatic, comprising the step of administering to the living body an amount of a compound of claim 1 which is effective for alleviation of said disease.

* * * * *

UNITED STATES PATENT AND TRADEMARK OFFICE
CERTIFICATE OF CORRECTION

PATENT NO. : 5,866,587
DATED : Feb. 2, 1999
INVENTOR(S) : G. Nanteuil, J. Paladino, G. Remond, G. Atassi, A. Pierre, G. Tucker, J. Bonnet, M. Sabatini It is certified that error appears in the above-indentified patent and that said Letters Patent is hereby corrected as shown below:

Column 4, line 12: "formula (IIa):" should read -- formula (I/a): --.

Column 4, line 56: At the end of the line after "formula", insert -- (I), --.

Column 21, lines 7 & 8: Correct to read -- The expected product is obtained according to the process described in Example 1, starting from Spinacine. --

Column 24, line 15: Between "fused" and "ring", insert -- furan --.

Column 24, line 26: "A compound wherein $R_5$" should read -- A compound of claim 1 wherein $R_5$ --.

Signed and Sealed this

Sixth Day of July, 1999

Attest:

Q. TODD DICKINSON

*Attesting Officer*    Acting Commissioner of Patents and Trademarks